(12) United States Patent
Tseng et al.

(10) Patent No.: US 9,308,233 B2
(45) Date of Patent: *Apr. 12, 2016

(54) EXTRACT OF ADLAY BRAN AND USES THEREOF

(71) Applicant: JOBEN BIO-MEDICAL CO., LTD., Pingtung County (TW)

(72) Inventors: Huang-Chung Tseng, Pingtung County (TW); Giao-Zhi Huang, Pingtung County (TW); Tung-An Chia, Pingtung County (TW)

(73) Assignee: JOBEN BIO-MEDICAL CO., LTD., Pingtung County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/613,094

(22) Filed: Feb. 3, 2015

(65) Prior Publication Data

US 2015/0147416 A1    May 28, 2015

Related U.S. Application Data

(62) Division of application No. 14/539,501, filed on Nov. 12, 2014, now Pat. No. 8,986,754, which is a division of application No. 13/839,538, filed on Mar. 15, 2013, now Pat. No. 8,911,800.

(30) Foreign Application Priority Data

Dec. 20, 2012  (TW) .............................. 101148568 A

(51) Int. Cl.
   *A01N 65/00*  (2009.01)
   *A61K 36/8994*  (2006.01)

(52) U.S. Cl.
   CPC .................................. *A61K 36/8994* (2013.01)

(58) Field of Classification Search
   CPC ....................................................... A61K 36/00
   USPC ......................................................... 424/725
   See application file for complete search history.

(56) References Cited

PUBLICATIONS

Office action issued on Oct. 8, 2015 for the corresponding Taiwan, R.O.C. Patent Application No. 101148568.
Search report issued on Oct. 8, 2015 for the corresponding Taiwan, R.O.C. Patent Application No. 101148568.
Translation of the search report issued on Oct. 8, 2015 for the corresponding Taiwan, R.O.C. Patent Application No. 101148568.
Anti-inflammatory effect of extract of adlay bran and uses in reducing the side effects of radiation therapy for breast cancer patients, Mar. 5, 2012, http://www.gohomer.com.tw/item03/shownews.aspx?id=308&page=0.

*Primary Examiner* — Michael Meller
(74) *Attorney, Agent, or Firm* — WPAT, P.C., Intellectual Property Attorneys; Anthony King

(57) ABSTRACT

The present invention provides a composition comprising extract of adlay bran, wherein the adlay bran extract comprises C1 to C7 alcohol extract of adlay bran (A) and carbon dioxide supercritical fluid extract of adlay bran (B). Preferably, the extract of adlay bran has effects in treating a skin and/or subcutaneous tissue disease and in lowering interleukin (IL)-1α, interleukin-1β, interleukin-6, tumor necrosis factor (TNF)-α, interleukin-8, prostaglandin-2 (PGE2) and/or C-Reactive Protein (CRP).

1 Claim, 14 Drawing Sheets

EXTRACT OF ADLAY BRAN AND USES THEREOF

BACKGROUND OF THE INVENTION

1. Field of the Invention

The invention relates to extract of adlay bran and uses thereof; more particularly, the uses in treating a skin and/or subcutaneous tissue disease and lowering interleukin (IL)-1α, interleukin-1β, interleukin-6, tumor necrosis factor (TNF)-α, interleukin-8, prostaglandin-2 (PGE2) and/or C-Reactive Protein (CRP).

2. Description of the Related Art

The skin is the largest organ in the human body and is the main barrier between the body and the environment, and is the first line of defense from pathogens and physical and chemical stresses or stimulations. The skin not only provides the physical and chemical protection, but also is an immune organ that can effectively cause passive and active immune response, thereby protecting the human body.

From outside to inside, the skin has a three-layer structure composed of the epidermis, the dermis and the subcutaneous tissue. The outmost layer epidermis is responsible for protection functions; the dermis layer inside the epidermis layer is the most important part of the skin, and is responsible for supporting the epidermis and interlaces with various fibers to form a support net, and blood vessels, nerves, sebaceous glands, sweat glands and hair follicles are distributed in the dermis layer; the innermost layer of the skin is the subcutaneous tissue, which in general refers to the deep layer of the dermis of vertebrates, and in narrow sense refers to the adipose connective tissues between the dermis and skeleton and muscles below the dermis The subcutaneous tissue mainly formed by fat cells has no obvious boundary with the dermis, and is responsible for blocking and absorbing vibration and providing a source of energy. The subcutaneous tissue is a main site for fat metabolism.

The skin and/or the subcutaneous tissue may have various diseases due to some congenital or acquired factors, resulting in discomfort of patients, and changes in appearance cause psychological burdens on patients. However, the currently adopted skin and/or subcutaneous tissue agents are steroids or acidic agents, and great side effects may be caused by improper use, so use of the existing agents are not an appropriate treatment.

In the skin and/or subcutaneous tissue diseases, damages caused by radiation therapy is one of the important types, and the radiation therapy always induces side effects such as radiation dermatitis, fatigue, radiation pneumonia and lymphedema (McCormick et al., 1989, Int J Radiat Oncol Biol Phys., 17:1299-1302; Lingos et al., 1991, Int. J. Radiat. Oncol. Biol. Phys., 21:355-360; Taylor et al., 1995, Int J. Radiat. Oncol. Biol. Phys., 31:753-764; Gorodetsky et al., 1999, Int. J. Radiat. Oncol. Biol. Phys., 45:893-900; Erickson et al., 2001, J. Natl. Cancer Inst, 93:96-111). With breast cancer as an example, about 50% to 60% breast cancer patients need radiation therapy after operation. After operation resection and systemic chemotherapy, the side effects such as hair loss, neutropenia, nausea and vomiting always occur in the patients. As a result, the patients may evade or refuse the treatment because of fear. The medical community has made some improvements in the treatment equipment and technology to reduce the side effects of the radiation therapy. As for skin erythema and pigmentation caused by radiation and some serious side effects such as ulcer in a minority of the patients, the medical community always tries to use some radiation protection agents such as Amifostine (Yuhas et al., 1980, Cancer Clin. Trials., 3:211-216). However, the agents are almost not used in the actual medical practice due to accompanying strong side effects, non-obvious effect, or high price. An agent that has the effect of radiation protection or radiation effect strengthening and can reduce the dose of radiation is still needed, so as to bring benefit for cancer patients receiving the radiation therapy.

Adlay (Coix lachryma-jobi L. var. ma-yuen Stapf) seeds, also called Job's tears, are a component of traditional Chinese medicine (TCM) and have long been used as an anti-inflammatory agent to treat warts, chapped skin, rheumatism, and neuralgia (Li, S. C. Pen-t'sao kangmu (Systematic Pharmacopoeia); China, 1596). A recent study showed that dehulled adlay (DA) modulated the microbiota in the intestinal tract of rats (Chiang, W; Cheng, C.; Chiang, M.; Chung, K. T. J. Agric. Food Chem. 2000, 48, 829-832.). Also, the anti-inflammatory and antioxidative effects of adlay were elucidated in vitro (Lee, M. Y; Tsai, S. H.; Kuo, Y. H.; Chiang, W. Food Sci. Biotechnol. 2008, 17, 1265-1271; Kuo, C. C.; Shih, M. C.; Kuo, Y H.; Chiang, W. J. Agric. Food Chem. 2001, 49, 1564-1570). Contents of various potent compounds in adlay seeds from different origins were quantified (Wu, T. T.; Charles, A. L.; Huang, T. C. Food Chem. 2007, 104, 1509-1515). Several phenolic antioxidants were isolated from adlay seeds, and bioactive components in adlay seeds were found to be stable during processing (Hsu, H. Y; Lin, B. F.; Lin, J. Y; Kuo, C. C.; Chiang, W. J. Agric. Food Chem. 2003, 51, 3763-3769). Lignans and phenolic compounds were isolated from adlay hull (AH) in an assay-guided isolation (Kuo, C. C.; Shih, M. C.; Kuo, Y H.; Chiang, W. J. Agric. Food Chem. 2001, 49, 1564-1570). Flavanone and several phenolic acids were isolated from anti-inflammatory fractions of adlay seeds (Huang, D. W; Kuo, Y. H.; Lin, F. Y; Lin, Y L.; Chiang, W J. Agric. Food Chem. 2009, 57, 2259-2266; Huang, D. W; Chung, C. P.; Kuo, Y H.; Lin, Y L.; Chiang, W. J. Agric. Food Chem. 2009, 57, 10651-10657; Chen, H. J.; Chung, C. P.; Chiang, W; Lin, Y L. Food Chem. 2011, 126, 1741-1748). Phenolic alcohol in the adlay testa (AT) was reported to possess antiallergic activity (Chen, H. J.; Shih, C. K; Hsu, H. Y; Chiang, W. J. Agric. Food Chem. 2010, 58, 2596-2601). In addition, DA and adlay bran (AB) were shown to retard carcinogenesis through an anti-inflammatory pathway (Shih, C. K; Chiang, W; Kuo, M. L. Food Chem. Toxicol. 2004, 42, 1339-1347; Li, S. C.; Chen, C. M.; Lin, S. H.; Chiang, W; Shih, C. K J. Sci. Food Agric. 2011, 91, 547-552), and ferulic acid was regarded as the active component in a further investigation (Chung, C. P.; Hsu, H. Y; Huang, D. W; Hsu, H. H.; Lin, J. T; Shih, C. K; Chiang, W. J. Agric. Food Chem. 2010, 58, 7616-7623).

Although there are many uses of adlay seeds reported, various applications of extract of adlay seeds remain to be developed.

SUMMARY OF THE INVENTION

In the present invention, extract of adlay bran has effects in treating a skin and/or subcutaneous tissue disease and in lowering interleukin-1α, interleukin-1β, interleukin-6, tumor necrosis factor-α, interleukin-8, prostaglandin-2 and/or C-Reactive Protein. In particularly, the extract of adlay bran provides radiation protection or enhances radiation efficacy to reduce the dose of radiation and further to benefit cancer patients receiving the radiation therapy.

The present invention provides a composition comprising extract of adlay bran, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The invention also provides a method for treating a skin and/or subcutaneous tissue disease in a subject, which comprises administering to said subject an effective amount of extract of adlay bran and optionally a pharmaceutically acceptable carrier or excipient, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The invention also provides use of extract of adlay bran in the manufacture of a medicament of the treatment of a skin and/or subcutaneous tissue disease, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The invention further provides a method for lowering interleukin-1α, interleukin-1β, interleukin-6, tumor necrosis factor-a, interleukin-8, prostaglandin-2 and/or C-Reactive Protein in a subject, which comprises administering to said subject an effective amount of extract of adlay bran and optionally a pharmaceutically acceptable carrier or excipient, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The invention also provides use of extract of adlay bran in the manufacture of a medicament of lowering interleukin-1α, interleukin-1β, interleukin-6, tumor necrosis factor-a, interleukin-8, prostaglandin-2 and/or C-Reactive Protein, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

DETAILED DESCRIPTION OF THE INVENTION

Figure 1:
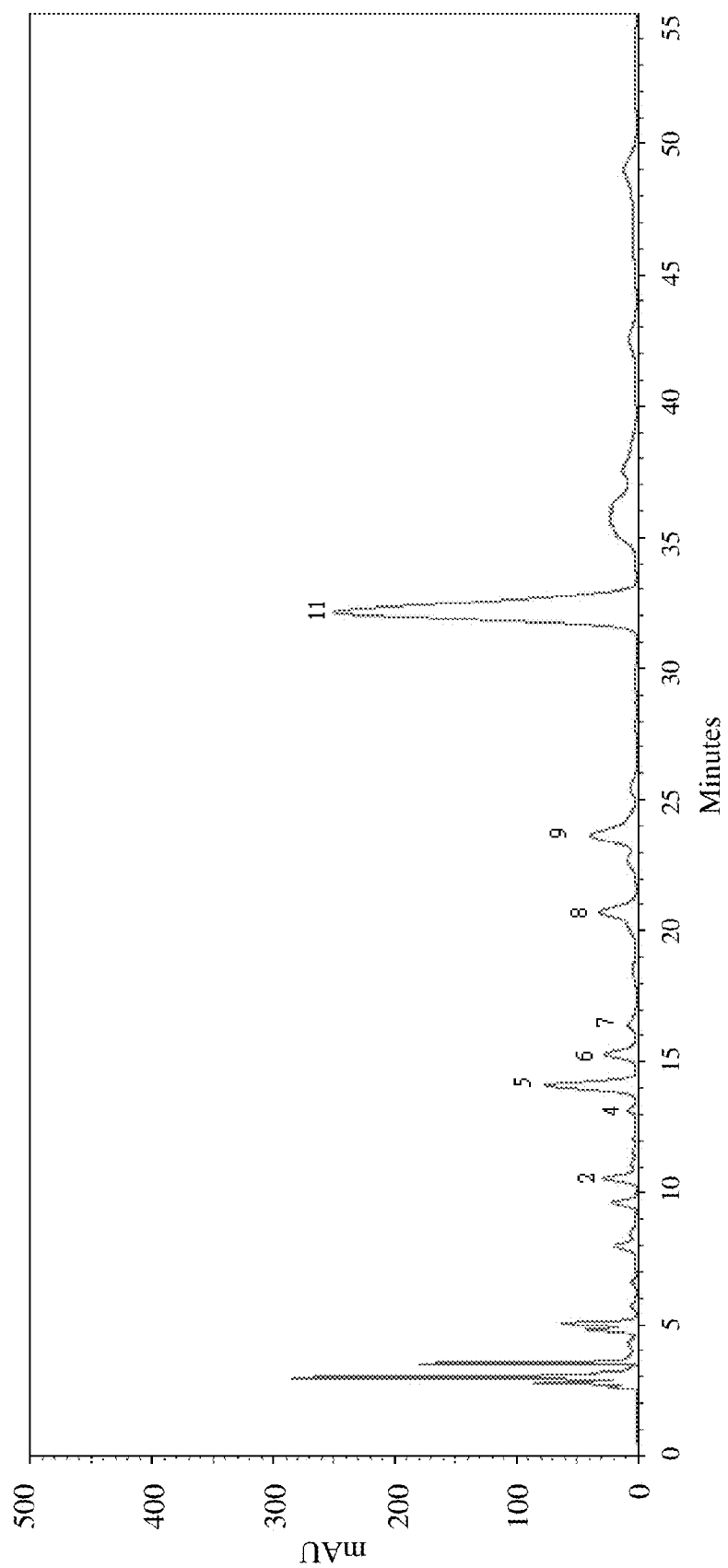
FIG. 1 illustrates the HPLC spectrogram of the C1 to C7 alcohol extract of adlay bran (A) according to the invention.

The present invention provides a composition comprising extract of adlay bran, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the extract of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±10%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The composition according to the invention comprises the extract of adlay bran. The adlay bran according to the invention preferably is obtained from dehulled adlay seeds. The term "dehulled adlay seeds" as used herein refers to seeds of adlay without hulls, testas, coverings, shells, or pods. The manner of removing the hulls, coverings, shells or pods from the adlay seeds is well-known to artisans skilled in this field. In general, the dehulled adlay seeds comprises bran and endosperm, and the manner of obtaining the bran from the dehulled adlay seeds is well-known to artisans skilled in this field.

The adlay seeds referred to in this invention are not particularly limited. Preferably, the adlay belongs to *Gramineae* family, *Panicoideae* sub-family, and Coix species, or Poales order, Poaceae family, and Coix species. More preferably, the adlay is *Coix lachryma-jobi, Coix lachryma-jobi* L., *Coix lachryma-jobi* L. var. ma-yuen Stapf, *Coix agrestis Lour., Coix arundinacea Lam., Coix exaltata Jacq.*, or *Coix lacryma L.*

The extract of adlay bran according to the invention comprises the C1 to C7 alcohol extract of adlay bran (A) and the carbon dioxide supercritical fluid extract of adlay bran (B).

The term "C1 to C7 alcohol" as used herein refers to linear or branched, substituted or unsubstituted, mono- or poly-functional, and saturated or unsaturated alcohol; preferably unsubstituted, mono-functional and saturated alcohol. In one preferred embodiment of the invention, the C1 to C7 alcohol is selected from the group consisting of methanol, ethanol, n-propanol, isopropanol, n-butanol, iso-butanol, sec-butanol, tert-butanol, 1-pentanol, 2-pentanol, 3-pentanol, 2-methyl-1-butanol, 2-methyl-2-butanol, 3-methyl-2-butanol, 3-methyl-1-butanol, 2,2-dimethyl-1-propanol, 1-hexanol, 2,4-hexadiene-1-ol, 2-methyl-cyclopentanol, cyclohexanol, 1-heptanol, 2-heptanol, or cycloheptyl alcohol. More preferably, the C1 to C7 alcohol is methanol or ethanol; most preferably, the C1 to C7 alcohol is ethanol. The C1 to C7 alcohol can be used solely or in combinations.

The C1 to C7 alcohol as used herein is preferably an alcohol solution with a concentration of from about 49% (v/v) to about 99.9% (v/v); more preferably from about 75% (v/v) to about 99.9% (v/v); still more preferably from about 90% (v/v) to about 98.0% (v/v).

As used herein, the term "C1 to C7 alcohol extract of adlay bran (A)" refers to extract obtained by extracting the adlay bran with the C1 to C7 alcohol. The manner of extracting a part of a seed with a solution is well-known to artisans skilled in this field. In one preferred embodiment of the invention, the adlay bran is soaked in the alcohol solution for extraction; more preferably, the adlay bran is soaked in the alcohol solution and subjected to ultrasonic vibration extraction.

The temperature of extraction is preferably from about 10° C. to about 100° C.; more preferably from about 15° C. to about 50° C.; still more preferably from about 20° C. to about 40° C.

In one preferred embodiment of the invention, the C1 to C7 alcohol extract of adlay bran (A) is prepared according to a process comprising:
  (a) providing adlay bran;
  (b) cutting the adlay bran into small pieces; and
  (c) extracting the small pieces in step (b) with the C1 to C7 alcohol to obtain an extract.

According to the process of the invention, prior to step (b), the adlay bran is preferably dried.

In one preferred embodiment of the invention, step (b) further comprises blending the small pieces into powder. The manner of cutting and/or blending is well-known to artisans skilled in this field.

The ratio (w/v) of the adlay bran and the alcohol solution is not specifically restricted, and can be about 1:1 to about 1:10; preferably about 1:3 to about 1:8; and most preferably about 1:5.

In one preferred embodiment of the invention, the extraction step (c) can be repeated, and the extract is collected by merging.

Preferably, the process further comprises (d) obtaining a liquid fraction from the extract, and a solid fraction is removed. The manner of removing the solid fraction to obtain the liquid fraction is well-known to artisans skilled in this field.

Preferably, the process further comprises a condensing step.

The manner of condensing is well-known to artisans skilled in this field, such as by a reduced-pressure condenser.

The carbon dioxide supercritical fluid extract of adlay bran (B) according to the present invention refers to an extract obtained by extracting adlay bran with carbon dioxide supercritical fluid. The supercritical fluid refers to a homogenous fluid state finally obtained when the properties of gas and liquid get similar at a temperature higher than the critical temperature and a pressure higher than the critical pressure. Similar to gas, the supercritical fluid has compressibility, and similar to fluid, has the fluidity, and can be used for extraction; moreover, a commercial supercritical fluid extraction equipment is available, for example, NATEX, SEPAREX, UHDE and TAIWAN SUPERCRITICAL TECHNOLOGY Co., Ltd. provide commercial supercritical fluid extraction equipments, of which the specifications are generally indicated by the capacity of the extraction tank, such as 500 g to 2000 kg for selection, so that a suitable supercritical fluid extraction equipment can be selected according to requirements.

In one preferred embodiment of the invention, the carbon dioxide supercritical fluid extract of adlay bran (B) is extracted at a pressure of from about 150 bar to about 500 bar; more preferably from about 200 bar to about 400 bar; still more preferably from about 350 bar to about 380 bar.

In one preferred embodiment of the invention, the carbon dioxide supercritical fluid extract of adlay bran (B) is extracted at a temperature of from about 30° C. to about 80° C.; more preferably from about 40° C. to about 70° C.; still more preferably from about 50° C. to about 60° C.

In one preferred embodiment of the invention, the carbon dioxide supercritical fluid extract of adlay bran (B) is extracted with a flux of carbon dioxide supercritical fluid of from about 20 kg/h to about 50 kg/h;
more preferably from about 30 kg/h to about 45 kg/h; still more preferably from about 38 kg/h to about 40 kg/h.

In one preferred embodiment of the invention, the extraction time for the carbon dioxide supercritical fluid extract of adlay bran (B) is from about 40 minutes to about 100 minutes; more preferably form about 50 minutes to about 80 minutes.

In one preferred embodiment of the invention, the carbon dioxide supercritical fluid extract of adlay bran (B) is extracted in the existence of a co-solvent such as about 1% to about 10% of 95% ethanol.

Preferably, the carbon dioxide supercritical fluid extract further comprises a condensing step. The manner of condensing is well-known to artisans skilled in this field, such as by a reduced-pressure condenser.

According to the invention, the weight ratio of the C1 to C7 alcohol extract of adlay bran (A) to the carbon dioxide supercritical fluid extract of adlay bran (B) is from about 3:1 to about 1:4. In the range, the pharmaceutical effect in treating a skin and/or subcutaneous tissue disease is very effective; preferably, the ratio is from about 3:2 to about 1:2; more preferably, the ratio is about 3:2, about 3:1, about 1:2 or about 1:4.

In one preferred embodiment of the invention, the extract of adlay bran is subjected to a high performance liquid chromatography assay. The sample is prepared as a concentration of 1 g/ml by using acetone as a solvent and filtrated with a 0.45 µm filter. Twenty-µL filtrated sample os analyzed by Hitachi® analysis HPLC. The column is Reverse phase C18 column (250×4.6 mm i d ; YMC Co., INC), and the detector is photo-diode array detector. The column temperature is 40° C. The chromatograms are extracted at 280 nm. The mobile phase uses Solution A: 5% acetic acid in water; Solution B: 0.5% acetic acid in water/100% acetonitrile (1:1, v/v).

The gradient elution program is shown in Table 1.

TABLE 1

| Time (min) | Flux (mL/min) | Solution A (%) | Solution B (%) |
|---|---|---|---|
| 0 | 1.0 | 90 | 10 |
| 10 | 1.0 | 85 | 15 |
| 20 | 1.0 | 84 | 16 |
| 35 | 1.0 | 83 | 17 |
| 50 | 1.0 | 79 | 21 |
| 55 | 1.0 | 79 | 21 |

Figure 2:
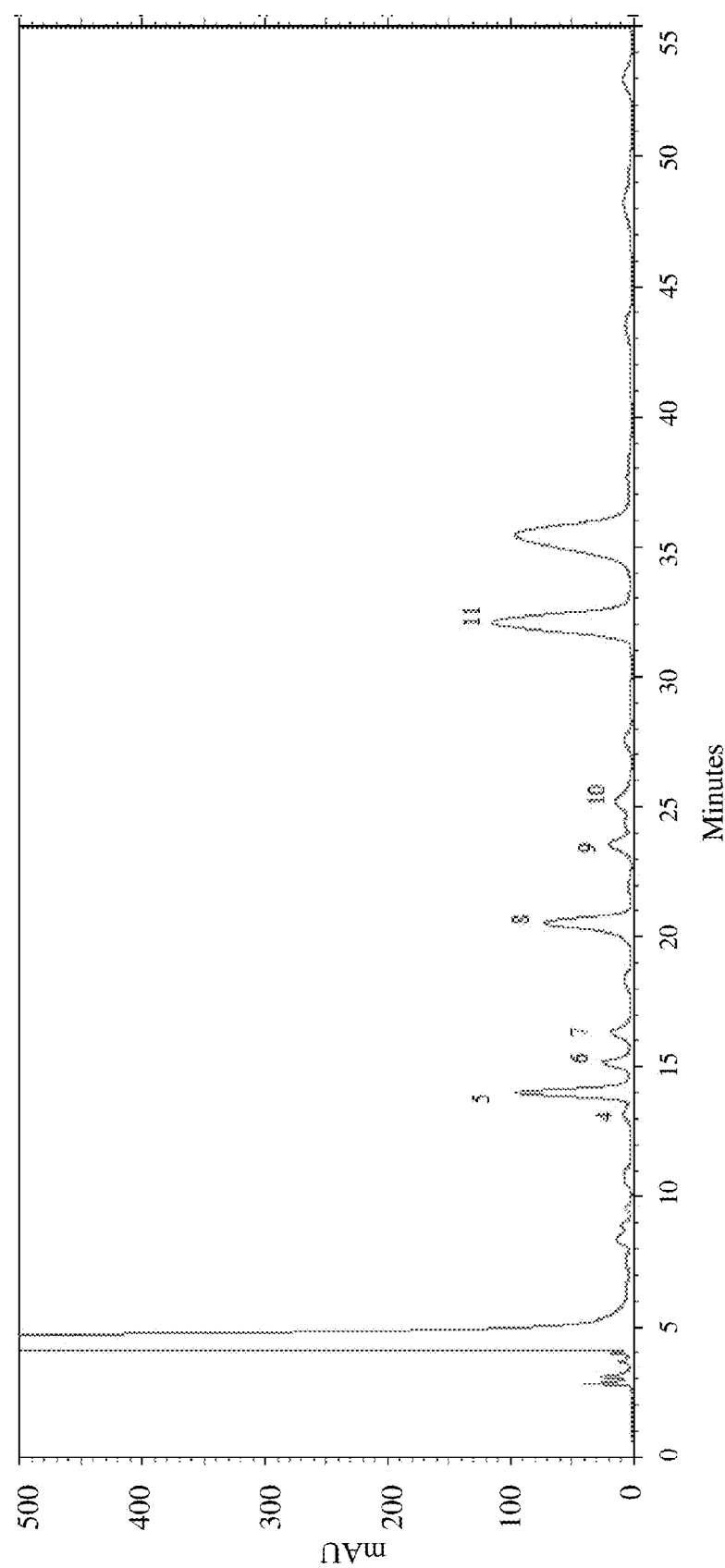
FIG. 2 illustrates the HPLC spectrogram of the carbon dioxide supercritical fluid extract of adlay bran (B) according to the invention.
Figure 3:
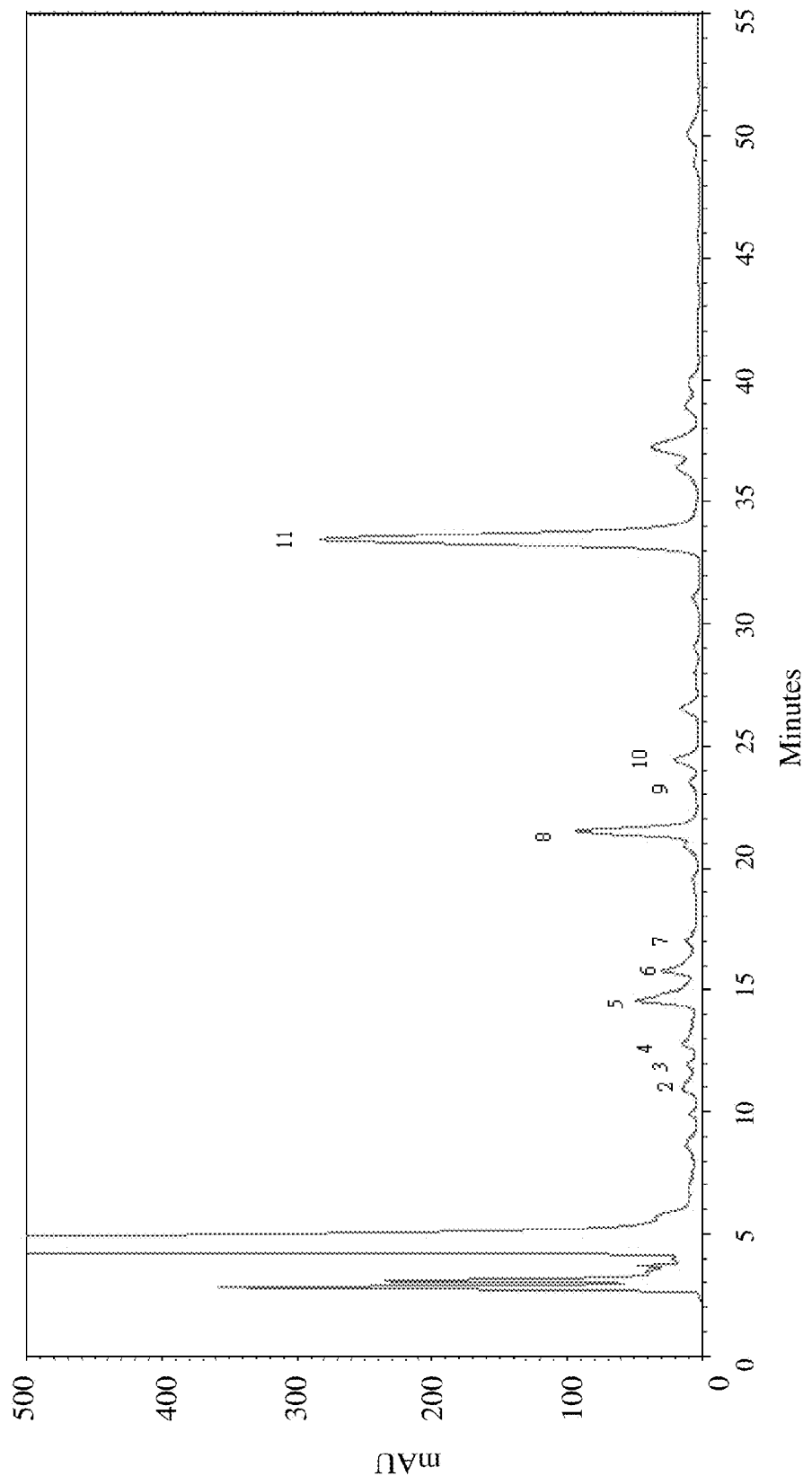
FIG. 3 illustrates the HPLC spectrogram of the extract of adlay bran according to the invention with the 1:4 weight ratio of the C1 to C7 alcohol extract of adlay bran (A) to the carbon dioxide supercritical fluid extract of adlay bran (B).

The spectrogram of the C1 to C7 alcohol extract of adlay bran (A) is shown in FIG. 1; the spectrogram of the carbon dioxide supercritical fluid extract of adlay bran (B) is shown in FIG. 2; and the spectrogram of the extract of adlay bran with the 1:4 weight ratio of the C1 to C7 alcohol extract of adlay bran (A) to the carbon dioxide supercritical fluid extract of adlay bran (B) is shown in FIG. 3. As shown in FIG. 3, the spectrogram obtained comprises peaks at retention time of about 12.5 minute to about 13.5 minute, about 14 minute to about 15 5 minute, about 15.5 minute to about 16.5 minute, about 21 minute to about 22.5 minute, and about 32 minute to about 35 minute.

The composition according to the invention is preferably a pharmaceutical composition, food composition or a cosmetic composition.

The pharmaceutical composition according to the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art; see paragraph [0037] for example.

The external route as used herein is also known as local administration, includes but is not limited to administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution. The aerosol composition may optionally contain additional formulation excipients well known in the art such as surfactants e.g. oleic acid or lecithin and cosolvents e.g. ethanol.

Topical preparations may be administered by one or more applications per day to the affected area; over the skin areas occlusive dressings may advantageously be used. Continuous or prolonged delivery may be achieved by an adhesive reservoir system.

The cosmetic composition according to the invention may be an aqueous phase formulation consisting essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, C3-C4 ketones and C2-C4 aldehydes, and glycerin. Such an aqueous formulation preferably is in a form of aqueous gel or hydrogel formulation. The hydrogel formulation comprises a thickening agent to thicken the liquid solution. Examples of the thickening agents include, but are not limited to, carbomers, cellulose base materials, gums, algin, agar, pectins, carrageenan, gelatin, mineral or modified mineral thickeners, polyethylene glycol and polyalcohols, polyacrylamide and other polymeric thickeners. The thickening agents which give the stability and optimal flow characteristics of the composition are preferably used.

The cosmetic composition according to the present invention may be in a form of emulsion or cream formulation. It can contain emulsifying surfactants. These surfactants may be chosen from anionic and nonionic surfactants. Reference may be made to the document "Encyclopedia of Chemical Technology, Kirk-Othmer", volume 22, pp.

333-432, 3rd edition, 1979, Wiley, for the definition of the properties and functions (emulsifying) of surfactants, in particular pp. 347-377 of said reference, for the anionic and nonionic surfactants.

The surfactants preferably used in the cosmetic composition according to the invention are chosen from: nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of C1-C6 alkyl glucose, and mixtures thereof; anionic surfactants: C16-C30 fatty acids neutralized with amines, aqueous ammonia or alkaline salts, and mixtures thereof. Surfactants which make it possible to obtain an oil-in-water or wax-in-water emulsion are preferably used.

The cosmetic composition according to the invention may further comprise an effective amount of a physiologically acceptable antioxidant selected from the group consisting of butylated p-cresol, butylated hydroquinone monomethyl ether, and a tocopherol.

The cosmetic composition according to the invention may further comprise natural or modified amino acid, natural or modified sterol compound, natural or modified collagen, silk protein or soy protein.

The cosmetic composition according to the invention are preferably formulated for topical application to keratin materials such as the skin, the hair, the eyelashes or the nails. They may be in any presentation form normally used for this type of application, especially in the form of an aqueous or oily solution, an oil-in-water or water-in-oil emulsion, a silicone emulsion, a microemulsion or nanoemulsion, an aqueous or oily gel or a liquid, pasty or solid anhydrous product.

The cosmetic composition according to the invention may be more or less fluid and may have the appearance of a white or colored cream, an ointment, a milk, a lotion, a serum, a paste, a mousse or a gel. It may optionally be topically applied onto the skin in the form of an aerosol, a patch or a powder. It may also be in solid form, for example, in the form of a stick. It may be used as care products and/or as makeup products for the skin. Alternatively, It may be formulated as shampoos or conditioners.

In known fashion, the cosmetic composition according to the invention may also contain additives and adjuvants that are common in cosmetics, such as hydrophilic or lipophilic gelling agents, preservatives, antioxidants, solvents, fragrances, fillers, pigments, odor absorbers and dyestuffs.

The extract of adlay bran can be added to a conventional food composition (i.e. the edible food or drink or precursors thereof) in the manufacturing process of the food composition. Almost all food compositions can be supplemented with the extract of adlay bran of the invention. The food compositions that can be supplemented with the extract of adlay bran of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The invention also provides a method for treating a skin and/or subcutaneous tissue disease in a subject, which comprises administering to said subject an effective amount of extract of adlay bran and optionally a pharmaceutically acceptable carrier or excipient, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The invention also provides use of extract of adlay bran in the manufacture of a medicament of the treatment of a skin and/or subcutaneous tissue disease, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The "the skin and/or subcutaneous tissue disease" as used herein refers to a disease occurring in the skin and/or subcutaneous tissue. In one preferred embodiment of the invention, the skin and/or subcutaneous tissue disease is selected from the group consisting of inflammation, hair follicle damage, skin atrophy, bruising, burn, cheilitis, dry skin, flushing, alopecia, hyperpigmentation, hypopigmentation, induration, fibrosis, injection site reaction, extravasation change, nail change, photosensitivity, pruritus, itching, rash, desquamation, acne, acneiform, dermatitis associated with radiation, erythema multiforme, hand-foot skin reaction, skin breakdown, decubitus ulcer, striae, telangiectasia, ulceration, and urticaria.

In one preferred embodiment of the invention, the skin and/or subcutaneous tissue disease is caused by radiation. Preferably, the radiation is radiation of the radiation therapy for treating a tumor. The tumor is preferably a breast tumor or a lung tumor.

The invention further provides a method for lowering interleukin-1α, interleukin-1β, interleukin-6, tumor necrosis factor-a, interleukin-8, prostaglandin-2 and/or C-Reactive Protein in a subject, which comprises administering to said subject an effective amount of extract of adlay bran and optionally a pharmaceutically acceptable carrier or excipient, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The invention also provides use of extract of adlay bran in the manufacture of a medicament of lowering interleukin-1α, interleukin-1β, interleukin-6, tumor necrosis factor-a, interleukin-8, prostaglandin-2 and/or C-Reactive Protein, wherein the extract of adlay bran comprises C1 to C7 alcohol extract of adlay bran (A) and carbon dioxide supercritical fluid extract of adlay bran (B), and the weight ratio of the C1 to C7 alcohol extract of adlay bran (A) to the carbon dioxide supercritical fluid extract of adlay bran (B) is from about 3:1 to about 1:4.

The following examples are given for the purpose of illustration only and are not intended to limit the scope of the present invention.

EXAMPLE 1

Animal Model

Drugs and reagents: Adlay seeds (C. lachrymajobi L., Taichung Shuenyu no 4, TCS4) are purchased from the farmers in Taichung County, Taiwan.

C1 to C7 alcohol extract of adlay bran (A): The shell and the seed coat of adlay are removed by using a mill, and adlay bran is milled into powder, immersed in 3 folders of 95% ethanol (w/v) at 25° C., and subjected to ultrasonic vibration extraction for 24 hours. Extracts of three times extraction are combined, and condensed at reduced pressure at 50° C., to obtain ethanol extract of adlay bran.

Carbon dioxide supercritical fluid extract of adlay bran (B): The shell and the seed coat of adlay are removed by using a mill, and adlay bran is milled into powder and fed into a stainless steel extraction inner tank, and then the inner tank is placed into an extraction tank of supercritical extraction equipment. The extraction conditions are: extraction pressure: 360 bar; extraction temperature: 55° C.; carbon dioxide flux: 38 to 40 kg/h; co-solvent: 2% of 95% ethanol; extraction time: 60 min. The extract is collected, and condensed by a reduced-pressure condenser.

Extract weight ratio: The feeding dose of the adlay bran extract is selected to be 100 mg/Kg and 100 μL/day, and the tube feeding volume is 100 μL/mouse. The adlay bran extract used in the experiments is suspended in 0.5% CMC (carboxymethyl cellulose) through ultrasonic vibration and is fed through a tube, and the mice are sacrificed at the 35th day. The 25 types of different feeding doses are obtained by combining the feeding dose of the C1 to C7 alcohol extract of adlay bran (A) being 0, 100, 200, 300 and 400 mg/kg and the feeding dose of the carbon dioxide supercritical fluid extract of adlay bran (B) being 0, 100, 200, 300, 400 mg/kg, and the tube feeding volume is 100 μL/mouse/day.

Figure 4:
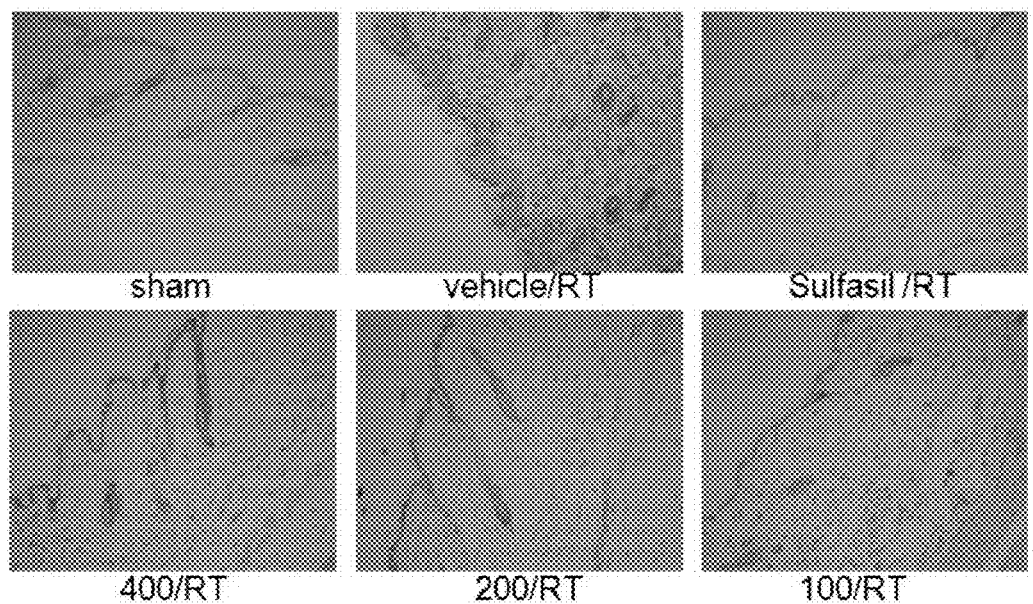
FIG. 4 illustrates the tissue pathological slices showing effects of the adlay capsules at different feeding doses or the agent Sulfasil for treating the skin injuries caused by clinical radiation therapy on the radiation therapy-caused mouse leg fur tissue damages. RT represents radiation therapy; sham represents without radiation therapy; and vehicle represents no carrier of adlay extract contained.

Discussion on activity and mechanism of extract against side effect of inflammation of the skin caused by radiation therapy of animal tumor: Adlay capsule is feed to animals through a tube (test group, extract A: extract B is 1:4), and the effect of different doses in alleviating the side effect of inflammation of the skin caused by radiation therapy is tested. In the animal model, mouse breast cancer cells (4T1, $1\times10^6$ cells/mouse) are implanted into BALB/c mouse leg, when the tumor diameter is about 4 mm, different doses of test samples are fed through a tube, and two days later, radiation therapy (irradiation 5 Gy each day, five day in total) is started and the adlay bran extract is fed through a tube every day, till the experiment is ended. In the experiment process, the tumor size and the weight are measured and the blood is sampled every five days. The agent Sulfasil for treating the skin injuries in current clinical radiation therapy is used as the control group. After the mice are sacrificed, tissue slices of the tumor radiation therapy part are made for epidermis and hair follicle tissue pathologic examination and determine the damage of the epidermis cells and fibroblasts in the epidermis tissue by adopting TUNEL assay, in combination with pathology, and detects expression of inflammation-related molecules such as NF-kB, COX-2, IL-1β and TNF-α by using immunostaining. The slice results are shown in FIG. 4.

Figure 5:
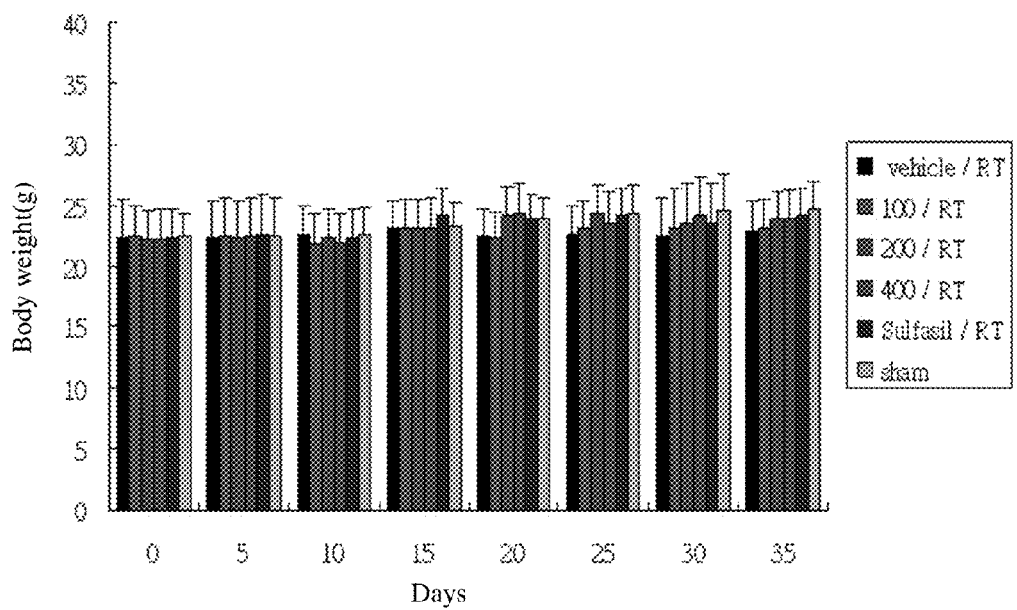
FIG. 5 illustrates the results of body weight changes of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.
Figure 6:
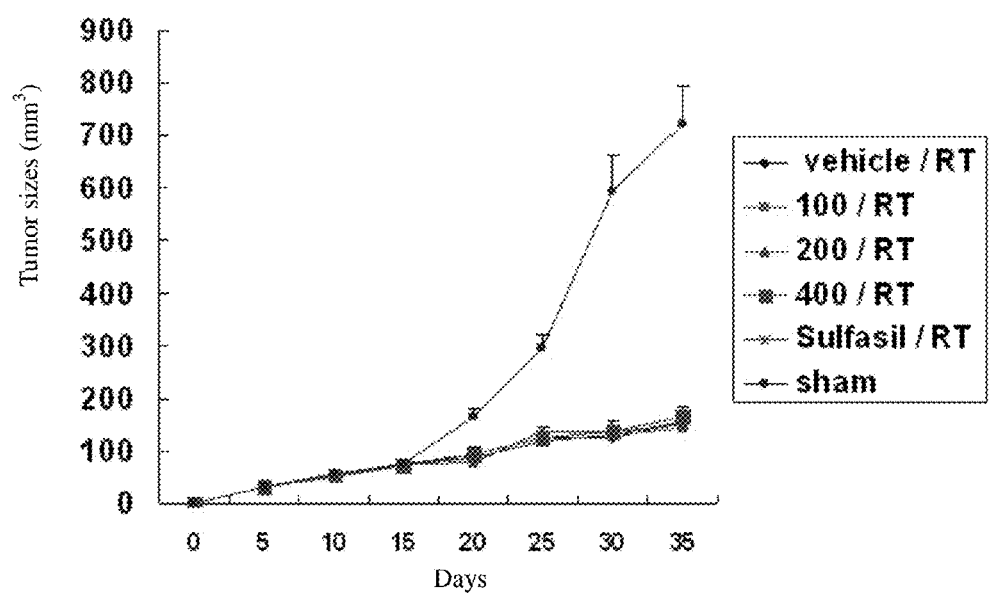
FIG. 6 illustrates the results of changes of the tumor volume of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.

Results of weight change are shown in FIG. 5, the test samples are administrated to the tumor animals when radiation therapy is administrated, and no significant difference in weight change exists between groups; it can be known from FIG. 6 that, the test samples are administrated to the tumor animals when radiation therapy is administrated, the tumor volume is significantly reduced, compared with the blank group, and no significant difference exists between the groups with radiation therapy administrated.

Figure 7:
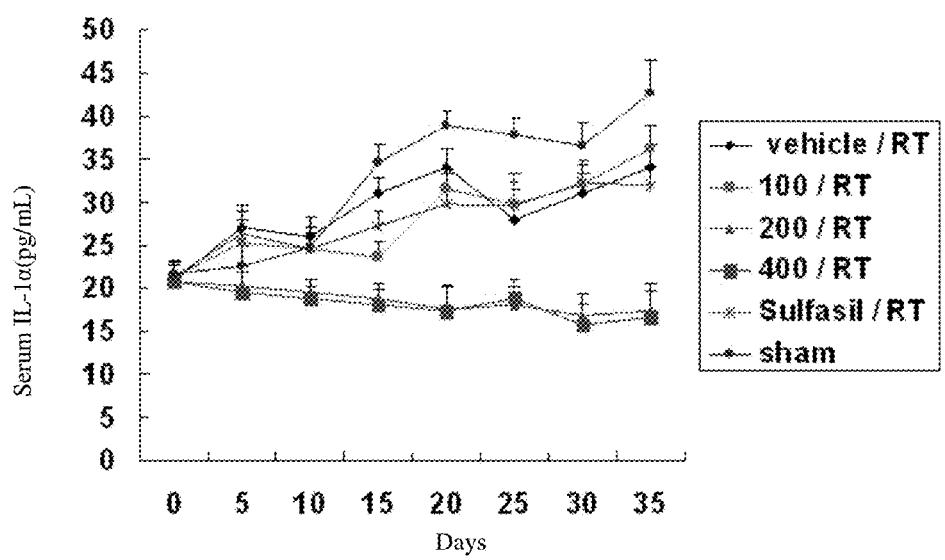
FIG. 7 illustrates the results of changes of serum IL-1α concentration of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.
Figure 8:
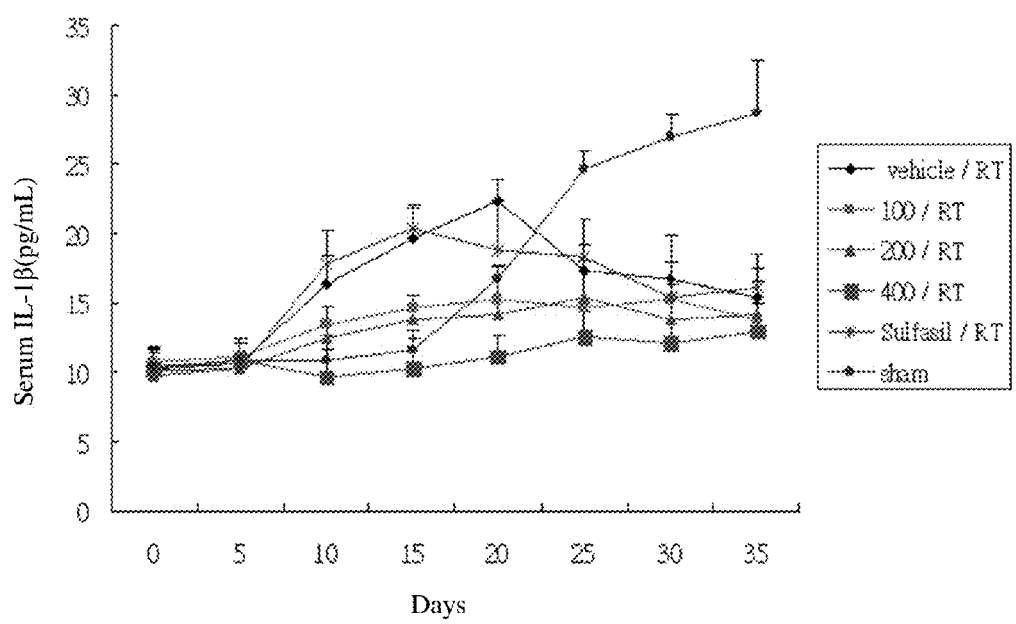
FIG. 8 illustrates the results of changes of serum IL-1β concentration of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.
Figure 9:
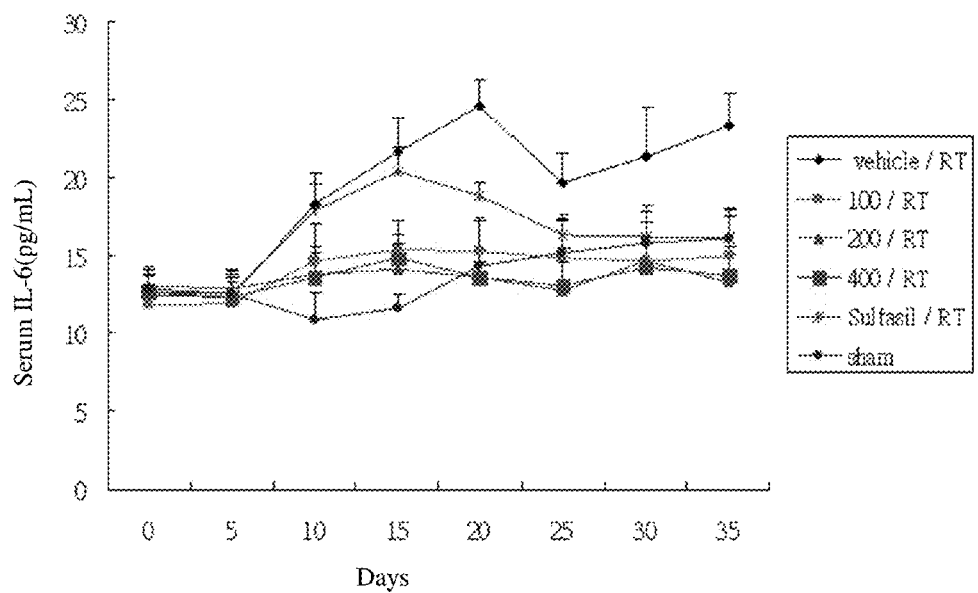
FIG. 9 illustrates the results of changes of serum IL-6 concentration of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.
Figure 10:
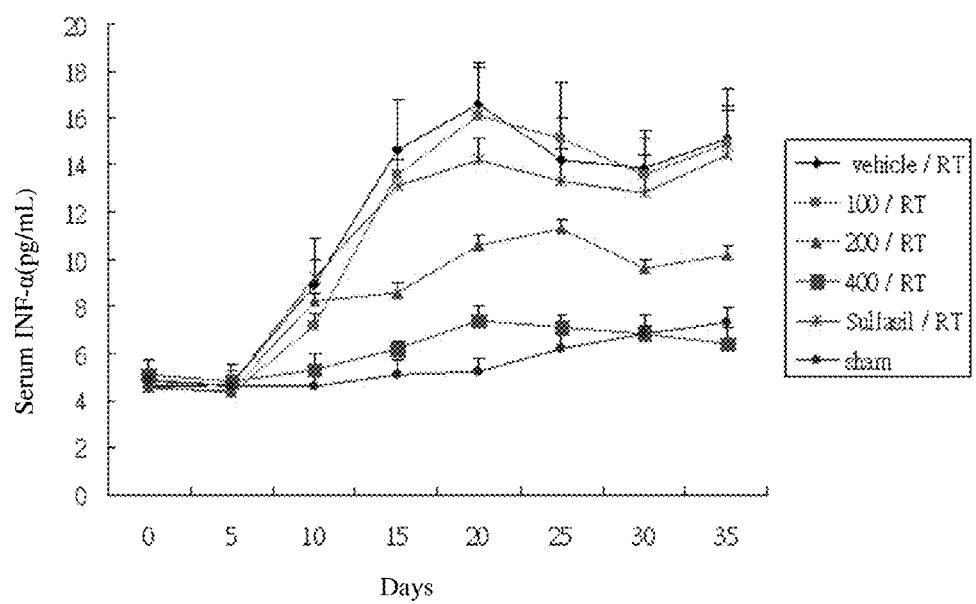
FIG. 10 illustrates the results of changes of serum TNF-α concentration of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.
Figure 11:
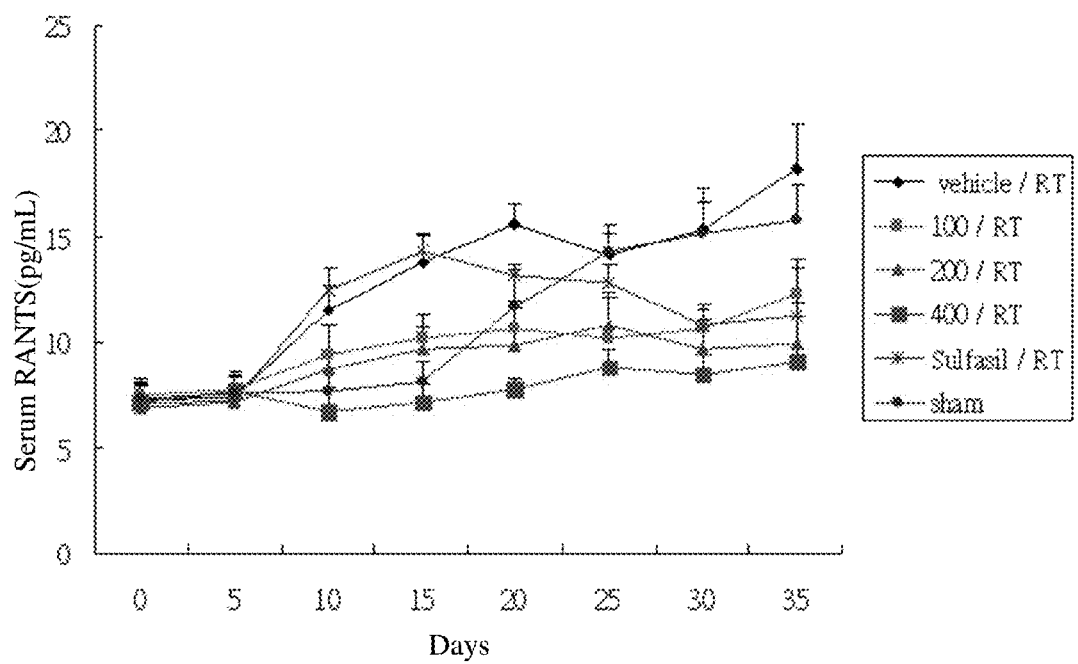
FIG. 11 illustrates the results of changes of serum IL-8 concentration of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.
Figure 12:
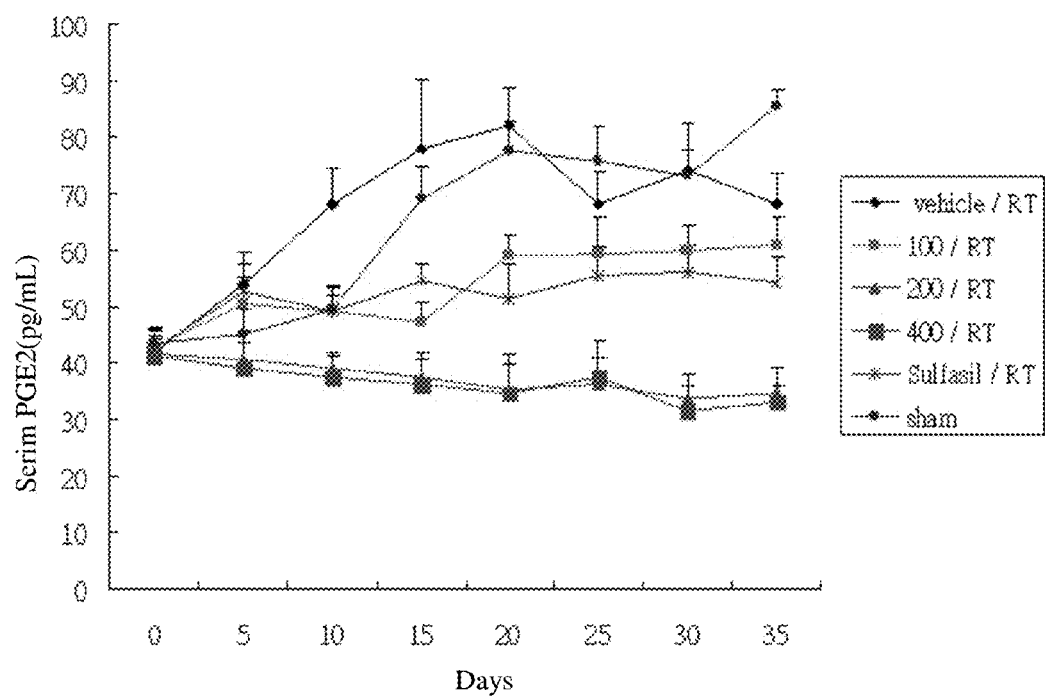
FIG. 12 illustrates the results of changes of serum PGE2 concentration of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.
Figure 13:
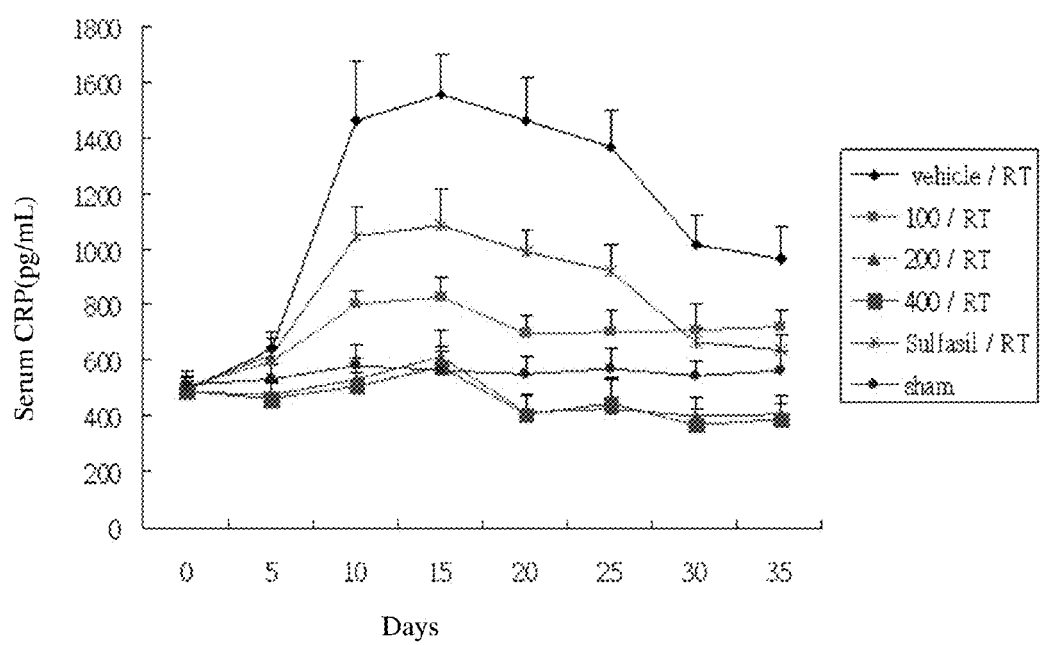
FIG. 13 illustrates the results of changes of serum IL-1α concentration of the tumor animals receiving the radiation therapy and at the same time, are fed with the adlay capsule of different concentrations or the agent Sulfasil for treating the skin injuries caused by clinical radiation therapy through a tube. RT represents radiation therapy; sham represents without radiation therapy; and vehicle represents no carrier of adlay extract contained.

In another aspect, adlay capsules (test group, extract A: extract B is 1:4) of 200 and 400 mg/kg significantly reduce the skin inflammation caused by radiation therapy, and at the same time, inhibit the increase of serum IL-1α (FIG. 7), IL-1β (FIG. 8), IL-6 (FIG. 9), TNF-α (FIG. 10), IL-8 (FIG. 11), PGE2 (FIG. 12) and CRP (FIG. 13) caused by radiation therapy; 100 mg/kg adlay capsule merely has significant inhibition effect on some indexes. It can be known from the results that, adlay capsules of 200 and 400 mg/kg have significant effect in reducing fur tissue injuries and inhibiting animal in vivo inflammatory factor indexes.

Figure 14:
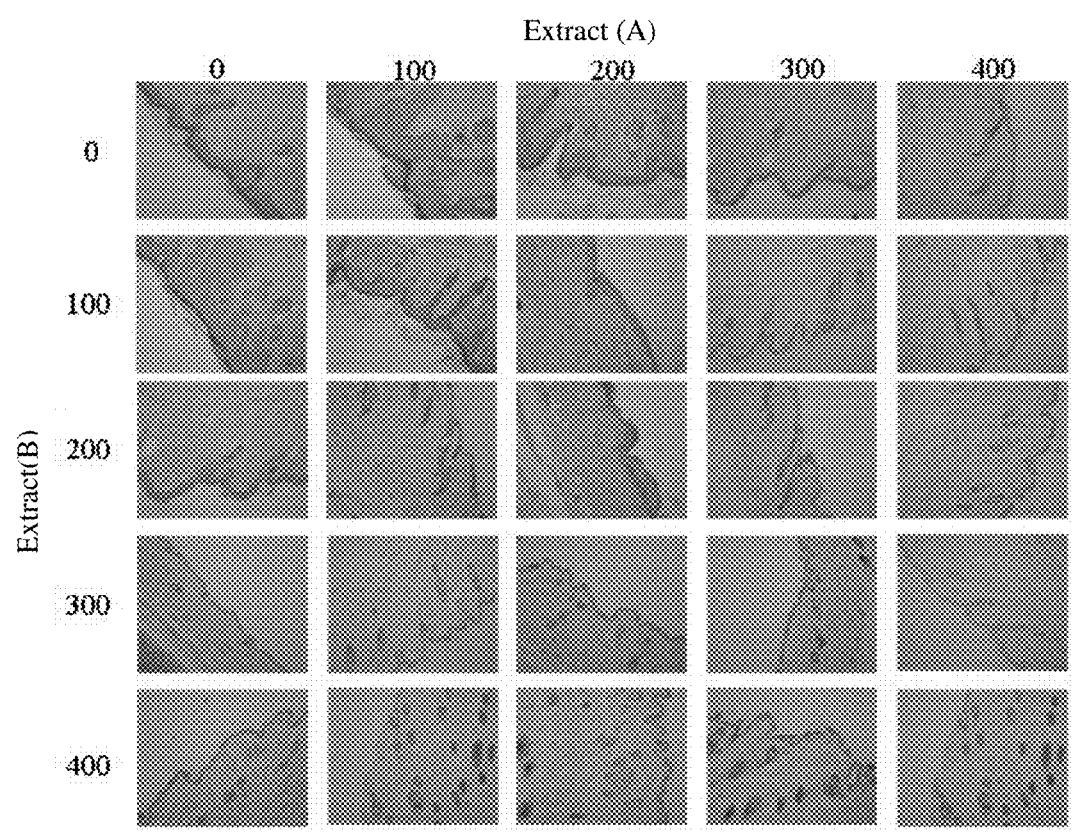
FIG. 14 illustrates the tissue pathological slices showing effects of 25 different feeding doses/combinations on the radiation therapy-caused mouse leg fur tissue damages. The horizontal axis and the vertical axis respectively represent the feeding dose/combination (mg/kg) of the C1 to C7 alcohol extract of adlay bran (A) and the carbon dioxide supercritical fluid extract of adlay bran (B). Each figure respectively illustrates the tissue pathological slices of fur tissues of mice that are fed with different doses through a tube in the process of radiation therapy of tumor.

Alleviating the skin and/or subcutaneous diseases caused by radiation therapy: The steps are performed as described in the safety evaluation, except that toxicity grading of in vivo epidermis response caused by tumor radiation therapy is evaluated every seven days in the study process. In the in vivo epidermis response toxicity grading method, the CTCAE (Common Terminology Criteria for Adverse Events v3.0) system that is most commonly used in toxicity evaluation in clinical treatment is adopted, and the grading is respectively performed through macroscopic observation and microscopic pathological tissue biopsy in clinical physiology, and quantitative evaluation is performed by using a skin response score table. Pathological tissue slices of the treatment part are made. The results are shown in FIG. 14.

In quantization of the skin response, CompuSyn (for Drug Combinations and for General Dose-Effect Analysis) software program is used to calculate the combination of synergistic effect of experimental materials in alleviating the skin responses and fur tissue injury caused by radiation therapy. The results are shown in Table 2:

TABLE 2

| Extract (B) (mg/kg) | Extract (A)(mg/kg) | uantitative evaluation of fur tissue injury | combination index |
|---|---|---|---|
| 100.0 | 300.0 | 0.96 | 0.68150 |
| 200.0 | 300.0 | 0.96 | 0.75281 |
| 400.0 | 100.0 | 0.96 | 0.48865 |
| 400.0 | 200.0 | 0.96 | 0.69204 |

As for the combination index (CI), according to definitions that CI value<1 is the addition effect, CI value=1 is the independent effect, and CI value>1 is the antagonistic effect, a combination of four best CIs (CI<0.8) obtained through screening in the experiment are shown in Table 2, indicating significant inhibition on fur tissue inflammation, in which extract A: extract B is in the range of 3:1 to 1:4.

It can be known from the results in Table 2 and FIG. 14 that, in the animal tumor radiation model in this embodiment, inflammation, hair follicle damage, hair loss, radiation dermatitis and/or hand/foot skin responses of the animals can be alleviated. Therefore, the extract of adlay bran according to the present invention can be used to treat the skin and/or subcutaneous tissue diseases, especially inflammation, hair follicle damage, hair loss, radiation dermatitis and/or hand/foot skin responses.

EXAMPLE 2

Human Experimentation of Alleviating Side Effects of Radiation Therapy on Breast Cancer Patients Two adlay capsules (test group, extract A : extract B is 1:4) or olive oil capsules (control group) (500 mg/capsule) are administrated after breakfast and dinner every day, and four capsules are administrated in total each day.

In this clinical trial, prospective and random grouping and double blind method are adopted, a test group and a control group are designed, and the clinical trail is carried out in two stages: At the first stage, response of common people to adlay capsule is first tested, in which two capsules (500 mg/capsule) are administrated after breakfast and dinner every day, four capsules are administrated in total each day, and the administration continues for four weeks. Blood examination is performed before test: including blood routine, liver function (including GOT and GPT), renal function (including BUN and CRTN), routine blood parameters (including cholesterol, HDL, LDL, TG and AC-sugar). After four-week continuous administration, the same blood examination is performed again, and after determining that no significant side effect exists, the second stage test is started: whether the adlay capsule can effectively reduce the skin responses caused by radiation when breast cancer patients receive radiation therapy and whether the quality of life is improved are determined; changes of immune function before and after the breast cancer patients receive radiation therapy are determined through blood examination, whether the adlay capsule can effectively improve the immune function is determined, and statistical analysis is performed on the clinical skin responses and physiological changes.

In the second stage test, breast cancer patients that meet the subject conditions are divided into two groups: one group is the test group, and the other group is the control group. For the test group, in the period of radiation therapy, two adlay capsules (500 mg/capsule) are administrated after breakfast and dinner every day, four capsules are administrated each day, and the administration continues for 5 to 7 weeks; for the control group, a substitute (placebo, the content is live oil) with the same package is administrated in the same administration manner The two groups are subjected to blood examination, the quality of life questionnaire and physical examination of the skin before and after treatment.

Number of patients:
First stage: 10 common people
Second stage: 80 breast cancer patients in the test group and the control group respectively.
170 subjects in total in the two stages.

Evaluation Method:
Safety test at the first stage: The subjects are subjected to blood examination for blood routine, liver function, renal function, and routine blood parameters, to determine whether serious abnormal responses are caused due to administration of the adlay capsule. The second stage: After a breast cancer patient agree to accept the test and signs the subject consent form after explanation, the patient is randomly divided into the test group or the control group, and is subjected to blood examination: including blood routine, liver function (including GOT and GPT), renal function (including BUN and CRTN), cytokine (including IL-1, IL-6 and IL-8) and routine blood parameters (including cholesterol, HDL, LDL, TG and AC-sugar), quality of life and fatigue questionnaire, physical examination of the skin (including: the pH value, skin surface moisture and grease, moisturizing function, color, temperature, elasticity and skin Doppler ultrasound). After radiation therapy is started, the skin responses and physical examination of the patient in the period of treatment are recorded every week, including the skin response and changes in color in the chest wall treatment. After radiation therapy is ended, the patients are subjected to blood examination and the quality of life questionnaire and physical examination of the skin the same as those before treatment.

Radiation Therapy:
Each breast cancer patient receives 5 to 7-week radiation therapy, and the subject needs to take the adlay capsule or substitute orally every day. In the radiation therapy, treatment range and volume are formulated through computer tomography, and the dose distribution and dose uniformity are obtained through a computer treatment operation system, and the skin responses and other side effects are recorded upon revisit of the patient every week.

Results:
Blood examination is performed before and after administration of the test product, the administration continues for four weeks, one patient has abdominal distension, and no adverse events or serious side effects exist. In the second stage test, 67 patients participate in subject screening, and 51 patients are enrolled, 16 patients among the subjects have no intention to participate in this program because of: allergy, edema and discomfort of lower extremity caused by chemical treatment, being unable to cooperate the treatment due to busy work, no intention, having taking too much drugs and being unable to participate the treatment, the rest patients sing the consent form, is subjected to blood examination, physical examination of the skin, photographic recording of the affected part, questionnaire and administration of the test product.

At the second stage, 2 patients have abdominal distension, and 1 patient has loose stool, in which one patient stops participating the test due to side effects such as abdominal distension, and one patient quits the test. According to the treatment plan, the period of treatment for each subject is about 5 to 7 weeks, and 160 subjects are expected to be enrolled. In order to improve the intension of the subject of participating this plan, increase the sample number, and increase the reliability of data collection, the ratio of the test group to the control group is adjusted from 1:1 to 2:1. The number of individual cases of which the data is analyzable is 27, and the analytical results are shown in Table 3 to Table 6.

Table 3 shows comparison of average values of blood examination of common people before and after administration of the adlay capsule at the first stage, in which no difference before and after administration exists between the test group and the control group, indicating that the adlay capsule will not affect the functions of liver and kidney.

TABLE 3

|  | Average pretest (±SD) | Average posttest (±SD) | p-value |
| --- | --- | --- | --- |
| Ages | 54.9 (11.36) | | |
| Height | 159.1 (4.31) | | |
| weight | 58.3 (6.57) | | |
| RBC | 4.4 (0.65) | 4.4 (0.79) | 0.648 |
| hemoglobin | 13.3 (1.30) | 13.3 (1.09) | 0.870 |
| WBC | 5.7 (1.22) | 5.6 (0.83) | 0.799 |
| Hct | 38.8 (3.45) | 39.5 (3.06) | 0.285 |
| platelet | 267.1 (29.13) | 265.7 (41.35) | 0.859 |
| BUN | 11.2 (3.46) | 12.0 (1.83) | 0.375 |
| creatinine | 0.6 (0.10) | 0.6 (0.13) | 0.670 |
| GOT | 26.4 (5.85) | 23.8 (5.27) | 0.045 |
| GPT | 25.2 (10.1) | 22.5 (9.64) | 0.158 |
| cholesterol | 195.8 (44.70) | 201.4 (33.07) | 0.523 |
| HDL | 51.7 (13.84) | 50.6 (11.39) | 0.393 |
| LDL | 117.5 (34.46) | 120.8 (25.63) | 0.688 |
| TG | 100.2 (52.45) | 105.8 (64.24) | 0.491 |
| ACsugar | 103.0 (24.21) | 109.6 (30.71) | 0.024 |

Table 4 shows grading of the skin response RTOG/EORTC indexes when breast cancer patients receive treatment, and it can be seen from the preliminary analysis of the results that, 3/14 (21.4%) of the patients in the test group have a skin response grade greater than 1, and 6/13 (46.2%) of the patients in the control group have a skin response grade greater than 1.

TABLE 4

|  | Experiment group (n = 14) | Control group (n = 13) | p-value |
| --- | --- | --- | --- |
| Skin reaction | | | 0.342 |
| Grade 0 | 4 (28.6%) | 1 (7.7%) | |
| Grade 1 | 7 (50.0%) | 6 (46.2%) | |
| Grade 2 | 3 (21.4%) | 5 (38.5%) | |
| Grade 3 | 0 (0.0%) | 1 (7.7%) | |
| Skin reaction | | | 0.173 |
| ≤Grade 1 | 11 (78.6%) | 7 (53.8%) | |
| >Grade 1 | 3 (21.4%) | 6 (46.2%) | |

Grade 0: No response
Grade 1: with follicles pale, erythema, hair loss, reduced sweating and dry peeling
Grade 2: with moderate erythema and peeling and edema of patchy infiltration, more obvious at the skin folds for most patients
Grade 3: with peeling and trauma of infiltration, and abrasion and bleeding
Grade 4: with necrosis, ulcer, spontaneous bleeding, and other symptoms
Grade 5: dead Table 5 shows clinical and pathological features of breast cancer patients after administration of the adlay capsule, in which no difference in distribution exists between the test group and the control group.

TABLE 5

| | Experiment group (n = 14) | Control group (n = 13) | p-value |
|---|---|---|---|
| Ages | 51.4 (±13.7) | 51.6 (±10.7) | 0.969 |
| clinical stage of primary tumor | | | 0.733 |
| 0 | 1 (7.1%) | 1 (7.7%) | |
| 1 | 3 (21.4%) | 1 (7.7%) | |
| 1b | 0 (0.0%) | 1 (7.7%) | |
| 1c | 3 (21.4%) | 5 (38.5%) | |
| 2 | 5 (35.7%) | 4 (30.8%) | |
| 3 | 1 (7.1%) | 0 (0.0%) | |
| is | 1 (7.1%) | 1 (7.7%) | |
| clinical stage of primary tumor | | | 0.340 |
| 1a | 3 (21.4%) | 1 (7.7%) | |
| 1b | 3 (21.4%) | 3 (23.1%) | |
| 1c | 3 (21.4%) | 5 (38.5%) | |
| 2 | 3 (21.4%) | 2 (14.3%) | |
| 3 | 2 (14.3%) | 0 (0.0%) | |
| is | 0 (0.0%) | 2 (14.3%) | |
| Pathological classification | | | 0.308 |
| Infiltrating ductal carcinoma | 13 (92.9%) | 10 (76.9%) | |
| Infiltrating lobular carcinoma | 1 (7.1%) | 1 (7.7%) | |
| Ductal carcinoma in situ | 0 (0.0%) | 2 (15.4%) | |
| Surgical classification | | | 0.511 |
| breast conserving surgery | 12 (85.7%) | 11 (84.6%) | |
| modified radical mastectomy | 0 (0.0%) | 1 (7.7%) | |
| Others | 2 (14.3%) | 1 (7.7%) | |
| Radiation therapy | | | 0.363 |
| conventional radiation therapy | 4 (28.6%) | 4 (30.8%) | |
| intensity modulated radiation therapy | 8 (57.1%) | 9 (69.2%) | |
| tomotherapy | 2 (14.3%) | 0 (0.0%) | |

Table 6 shows changes of blood examination before and after treatment of breast cancer patients after radiation therapy, in which no significant difference exists.

TABLE 6

| | Experiment group (n = 14) | Control group (n = 13) | p-value |
|---|---|---|---|
| RBC | | | 0.323 |
| Pretest | 4.12 (0.40) | 4.04 (0.40) | |
| Posttest | 4.37 (0.52) | 4.13 (0.43) | |
| Hgb | | | 0.310 |
| Pretest | 12.04 (1.72) | 12.11 (1.55) | |
| Posttest | 12.54 (1.25) | 12.20 (0.94) | |
| WBC | | | 0.719 |
| Pretest | 5.24 (2.06) | 5.74 (2.10) | |
| Posttest | 3.79 (0.90) | 4.04 (0.89) | |
| Hct | | | 0.219 |
| Pretest | 35.42 (4.45) | 35.56 (4.14) | |
| Posttest | 37.18 (3.17) | 35.92 (2.54) | |
| platelet | | | 0.160 |
| Pretest | 231.60 (84.74) | 273.54 (68.67) | |
| Posttest | 172.00 (46.44) | 179.15 (67.65) | |
| BUN | | | 0.179 |
| Pretest | 10.45 (3.05) | 11.86 (4.93) | |
| Posttest | 10.86 (3.59) | 10.67 (3.95) | |
| creatinine | | | 0.193 |
| Pretest | 0.57 (0.12) | 0.62 (0.17) | |
| Posttest | 0.59 (0.11) | 0.61 (0.14) | |
| GOT | | | 0.207 |
| Pretest | 25.86 (5.93) | 22.85 (5.40) | |
| Posttest | 25.50 (4.45) | 25.62 (10.45) | |
| GPT | | | 0.303 |
| Pretest | 24.14 (10.10) | 22.92 (11.18) | |
| Posttest | 22.93 (6.74) | 26.08 (15.75) | |
| Cho | | | 0.584 |
| Pretest | 196.43 (35.72) | 189.38 (29.11) | |
| Posttest | 181.79 (35.71) | 180.46 (24.44) | |
| HDL | | | 0.814 |
| Pretest | 46.30 (12.19) | 54.69 (14.73) | |
| Posttest | 45.57 (10.80) | 54.59 (11.03) | |
| LDL | | | 0.593 |
| Pretest | 121.26 (36.59) | 54.69 (27.13) | |
| Posttest | 111.35 (36.50) | 97.13 (27.36) | |
| TG | | | 0.256 |
| Pretest | 122.14 (60.31) | 100.69 (50.44) | |
| Posttest | 125.64 (51.51) | 161.62 (215.25) | |
| ACsugar | | | 0.866 |
| Pretest | 99.64 (10.67) | 103.62 (13.84) | |
| Posttest | 97.93 (14.12) | 101.38 (17.06) | |

The results of this embodiment show that, dry skin, induration, rash, desquamation, acne, erythema multiforme, skin breakdown and/or ulceration of the breast cancer patients can be alleviated; therefore, the extract of adlay bran according to the present invention can be used to treat the skin and/or subcutaneous tissue diseases, especially dry skin, induration, rash, desquamation, acne, erythema multiforme, skin breakdown and/or ulceration.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A method for treating a skin disorder or subcutaneous tissue disease which is caused by radiation therapy in a human in need thereof consisting essentially of administering to said human a therapeutically effective amount of a dehulled Coix lachryma-jobi L. seed extract which has been extracted with supercritical $CO_2$ and ethanol, wherein said pharmaceutical composition is in a form selected from the group consisting of a tablet, a pill, a capsule, a transdermal patch, a pessary, an ampoule, a retention enema bag, a pellet, and a microencapsulation to treat said skin disorder or subcutaneous tissue disease in said human in need thereof.

* * * * *